US00PP17672P3

(12) United States Plant Patent
Hofmann

(10) Patent No.: US PP17,672 P3
(45) Date of Patent: May 1, 2007

(54) APPLE TREE NAMED 'ROHO 3615'

(50) Latin Name: *Malus domestica Borkh.*
Varietal Denomination: ROHO 3615

(75) Inventor: Hans Hofmann, Hauptstr. 36, D-91094 Langensendelbach (DE)

(73) Assignee: Hans Hofmann, Langensendelbach (DE)

( * ) Notice: Subject to any disclaimer, the term of this patent is extended or adjusted under 35 U.S.C. 154(b) by 101 days.

(21) Appl. No.: 11/100,366

(22) Filed: Apr. 6, 2005

(65) Prior Publication Data

US 2006/0230478 P1 Oct. 12, 2006

(51) Int. Cl.
*A01H 5/00* (2006.01)

(52) U.S. Cl. ..... Plt./161

(58) Field of Classification Search ..... Plt./161
See application file for complete search history.

(56) References Cited

PUBLICATIONS

UPOV–ROM GTITM, Plant Variety Database, 2006/01, GTI Jouve Retrieval Software, Citation for *Malus* 'ROHO 3615' one page.*

* cited by examiner

*Primary Examiner*—Kent Bell
*Assistant Examiner*—June Hwu
(74) *Attorney, Agent, or Firm*—The Webb Law Firm

(57) ABSTRACT

A new and distinct *Malus domestica Borkh.* plant that produces apples having an excellent sugar-acid balance and keeping quality, suitable for use as a table and dessert fruit.

3 Drawing Sheets

Botanical classification: *Malus domestica Borkh.*
Varietal denomination: 'ROHO 3615'.

BACKGROUND OF THE INVENTION

The present invention comprises a new and distinct cultivar of apple tree botanically classified as *Malus domestica Borkh.* and known by the varietal name 'ROHO 3615'. The new variety was discovered in 2000 in Langensendelbach, Germany. The new variety is the result of a natural and stable branch mutation of 'Pinova' (U.S. Plant Pat. No. 11,601). The new variety exhibits similar disease resistance, fruit storage capacity, tree growth, fruit quality, and fruit size to 'Pinova', but exhibits a full red color. The full red color of 'ROHO 3615', especially of the apples ripened in the shadow of the trees, distinguishes the new variety from other *Malus domestica* varieties. Further, the fruit of the new variety ripens later than 'Gala' (U.S. Plant Pat. No. 3,637) and the taste of 'Gala' fruit is sweeter. However, 'Gala' is more susceptible to scab.

The new variety has been trial and field tested and has been found to retain its distinctive characteristics and remain true to type through successive propagations.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
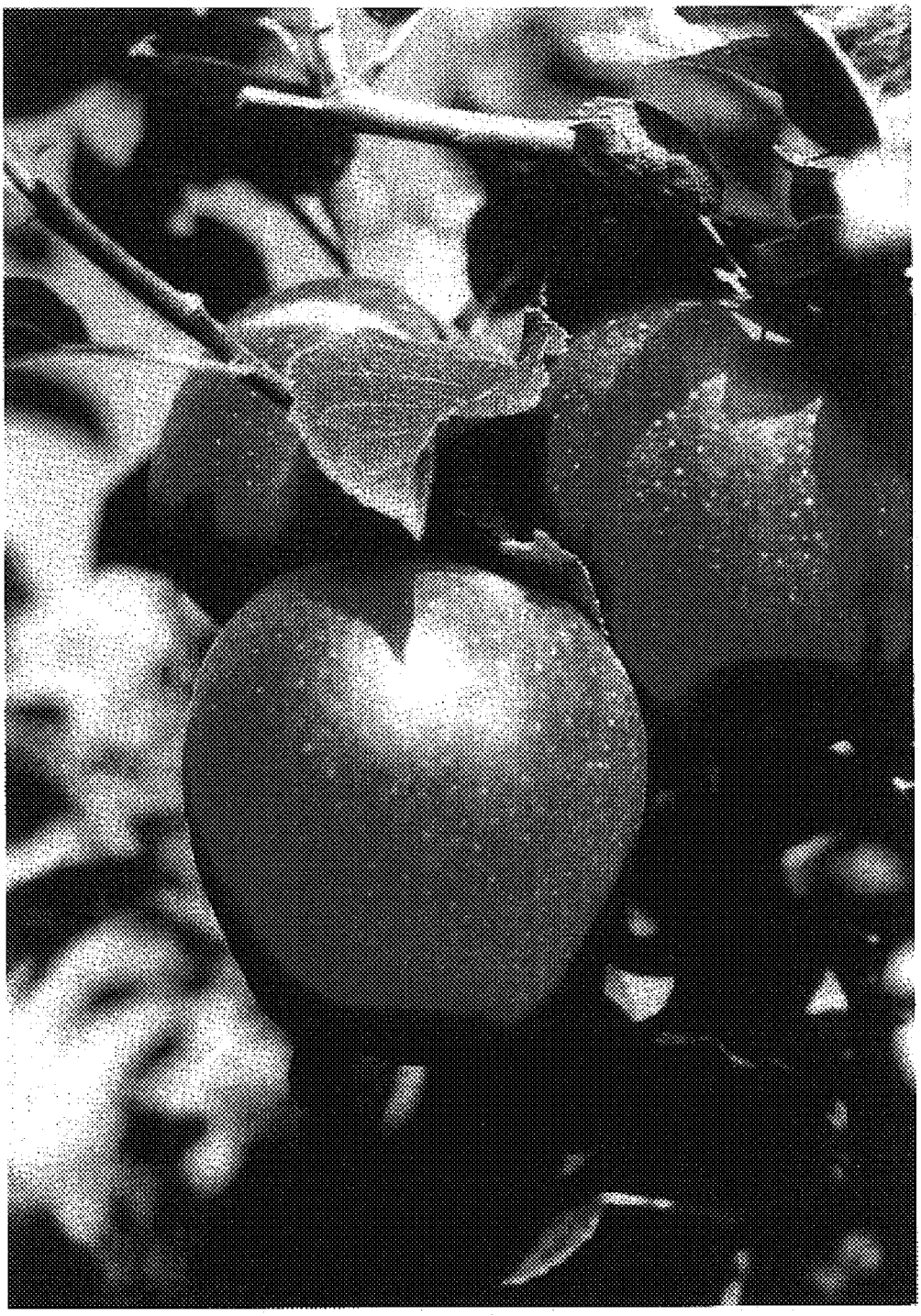
FIG. 1 shows the fruits of the new variety at maturity.
Figure 2:
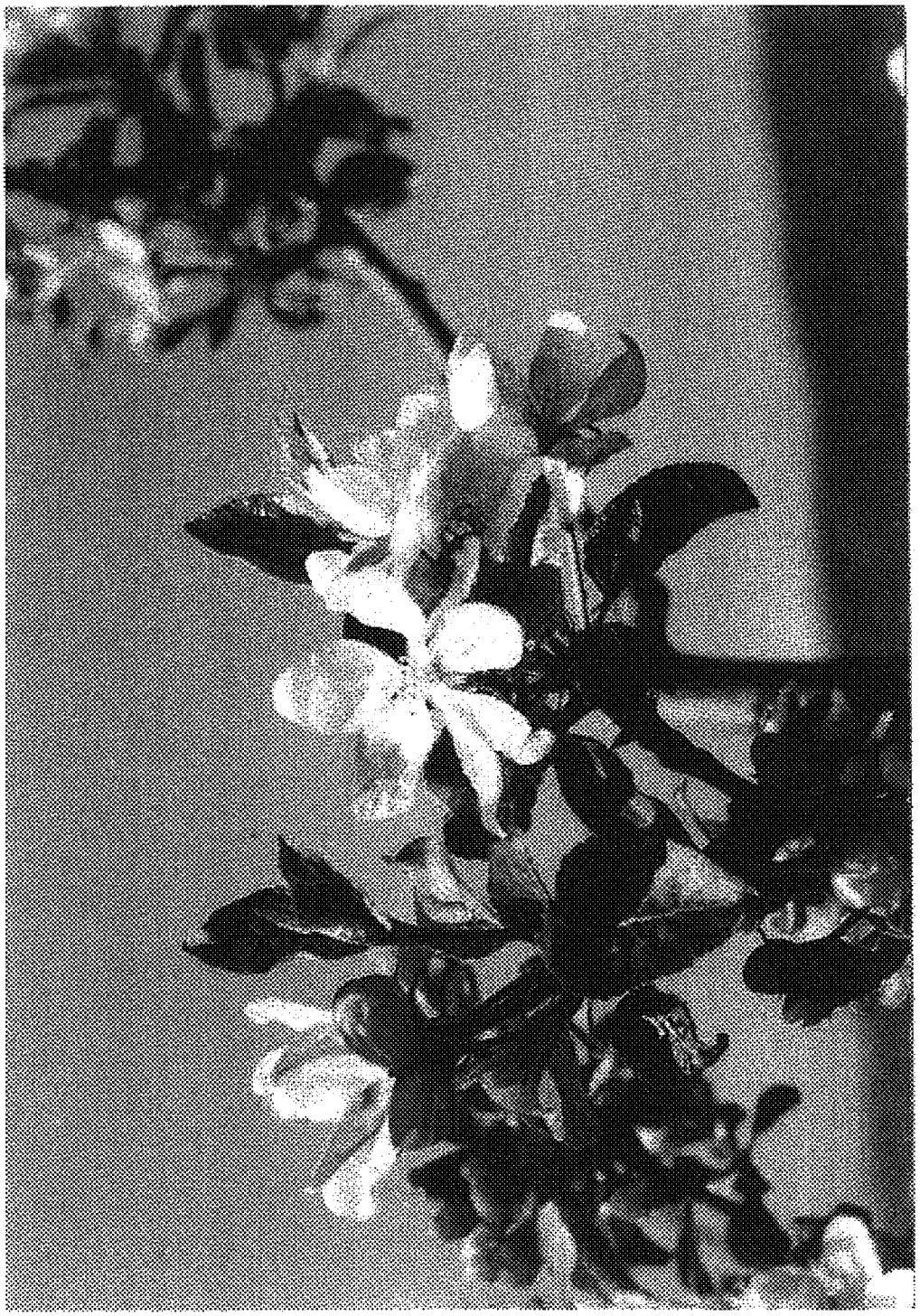
FIG. 2 shows the blooms of the new variety.
Figure 3:
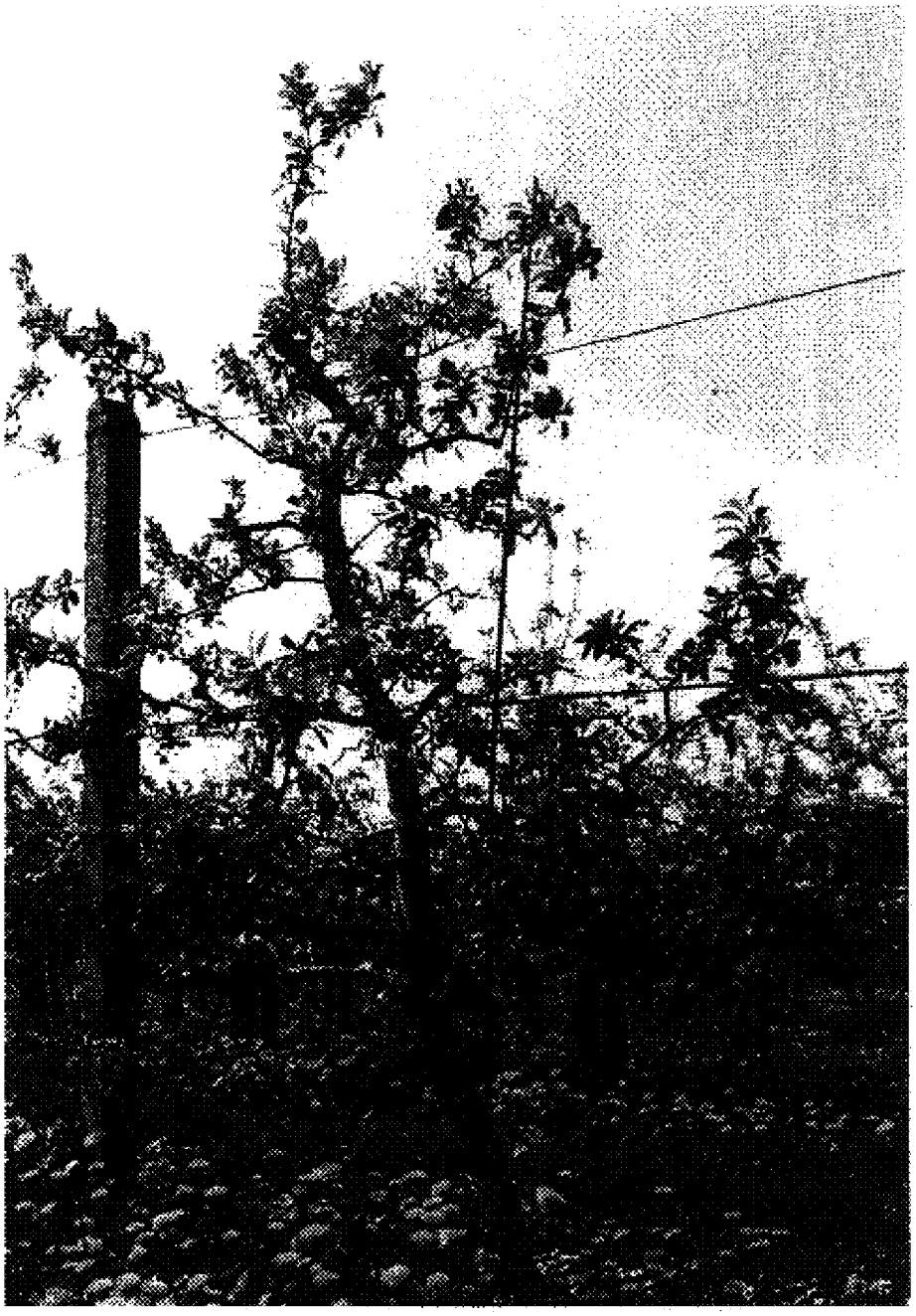
FIG. 3 shows an entire tree of the new variety.

The following detailed description sets forth the characteristics of the new cultivar. The data which defines these characteristics was collected by asexual reproductions by budding and grafting first carried out in Langensendelbach, Germany in 2000. The new variety was grafted on M9 Rootstock and grown in a planting system field. 'ROHO 3615' does not exhibit self-pollination. The color readings were taken in natural daylight. Color references are primarily to The R.H.S. Colour Chart of The Royal Horticultural Society of London.

TREE

Age: 3 years.
Size: 2.5 m high; small to medium in size.
Average spread: A 5 year-old tree grafted M9 rootstock is 1.8 cm.
Vigor: Dwarf.
Density: Not very dense with good ramification.
Form: Pyramidal.
Production: Very high and regular fruit production.
Growth type: Spindle bus; similar to 'Pinova'.
Bearing: Regular with no alternate bearing.
Trunk:
- *Size.*—4.8 cm in diameter at 80 cm high at 3 years on M9 Rootstock.
- *Surface texture.*—Smooth.
- *Bark color.*—166B.
- *Lenticels.*—Length: Average 5.0 mm (from 4.0–8.0 mm). Width: 1.0 mm (from 0.9–1.9 mm). Color: Pale brown, between 164C and 165D. Density: High.

Branches:
- *Diameter.*—Normal to thin in size; at 1 year of age the diameter is 8.0 mm.
- *Surface texture.*—Smooth.
- *Color.*— 1 year: 176A.
- *Form.*—Roundish in diameter with good ramification.
- *Average angle.*—60–75° in respect to the trunk.

*Bud arrangement.*—Mutual. Internode: Average of 3.0 cm (from 2.5–5.0 cm).

*Lenticels.*—Length: 2.0–3.5 mm. Width: 0.6–1.5 mm. Shape: Oblong to round. Density: Dense to very dense, similar to 'Pinova'. Color: 164C to 164D.

Leaves:

*Length.*—80.0–90.0 mm.

*Width.*—50.0–65.0 mm.

*Form.*—Ovate, like 'Pinova'.

*Base.*—Rounded.

*Apex.*—Tapering.

*Margin.*—Crenulate.

*Texture.*—Weak and wavy.

*Thickness.*—Normal.

*Pubescence.*—Upper surface: Weak. Lower surface: Weak to medium, younger leaves have more pubescence.

*Color.*—Young leaves: Upper surface: 144B. Lower surface: 144C to 145A. Mature leaves: Upper surface: 143A. Lower surface: 143C.

*Petiole.*—Shape: Straight. Length: 2.5–3.8 cm. Diameter: 1.8–2.2 mm; measured at the middle of a 1 year old shoot. Color: Between 141C and 143A.

*Veins.*—Venation type: Net-like. Color: Upper surface: 145A. Lower surface: 147D.

Flowers:

*Buds.*—Pedicels: Length: 2.5–3.5 cm. Diameter: 0.9–1.7 mm. Color: 133D to 138C. Bud (terminal): Length: 5.0–8.0 mm. Width: 3.5–5.0 mm. Shape: Triangular and tapering to the point. Color: 178A. Number of buds per spur: 3 to 8.

*Blooming time.*—Approximately May $5^{th}$ to the $18^{th}$ in Germany (similar to 'Gala').

*Blooming period.*—Long to very long (~15 days in Germany).

*Pollination requirements.*—Diploid; self-sterile; excellent pollinator.

*Number of flowers per cluster.*—5 to 9.

*Fragrance.*—Mild.

*Size.*—24 mm in diameter.

*Petals* (*no overlapping present*).—Number: 5. Length: 21 mm. Width: 9.0–11.0 mm. Shape: Oblong, tapering on the lower end. Margin: Entire. Texture and appearance: Solitary; rotate.

*Color.*—When opening: Upper surface: 56B. Lower surface: 57B–57C. When fully opened: Upper surface: 56B and 155B. Lower surface: 57D and 155C.

*Sepals.*—Shape: Tapering. Margin: Entire. Texture: Rough. Length: 5.0–6.0 mm. Width: 1.3–1.8 mm. Color: Upper surface: 144B. Lower surface: 144C.

*Stamens.*—Number (per flower): 13–15. Filament length: 4.0–6.0 mm.

*Anthers.*—Shape: Oblong. Length: 1.8–2.1 mm (average of 2.0 mm). Color: 3D.

*Pollen.*—Color: 17A to 17C. Amount (generally): Heavy.

*Pistils.*—Length: About 7.0–10.0 mm; variable.

*Style.*—Length: 6.0 mm. Color: 8C to 9D.

*Stigma.*—Shape: Rounded. Color: 1B to 2B.

Fruit:

*Maturity when described.*—Fully ripened.

*Date of picking.*—The second weak of October.

*Size.*—Axial diameter: Average 69.0 mm (from 64.0 to 71.0 mm). Transverse diameter: Average 76.0 mm (from 70.0 to 80.0 mm).

*Average weight.*—160 to 170 g on fruit approximately 75 mm in diameter.

*Form.*—Conical.

*Cavity.*—Shape: Flat. Depth: 7.0 mm. Breadth: 19.0 to 21.0 mm.

*Basin.*—Shape: Medium to deep. Depth: 13.0 mm. Width: 26.0 mm.

*Calyx.*—Closed.

Skin:

*Thickness.*—Thin and firm.

*Texture.*—Fine, with rare instances of minor russeting in the basin.

*Tendency to crack.*—No cracking.

*Color.*—46A to 46B.

*Ground color.*—151A, changing later to 12C to 13C.

*Bloom.*—Not present.

*Lenticels.*—Color: 20D to 23D. Length: 2.5 mm. Width: 2.0 mm.

Flesh:

*Aroma.*—Mild.

*Color.*—8D to 9D.

*Texture.*—Firm; juicy; fine.

*Eating quality.*—Excellent; well balanced sugar-acid content; sweet with a hint of sour; very good flavor.

Core:

*Bundle area.*—Medium to wide; with a visible bundle.

*Capillary area.*—Clear; medium to large.

*Calyx tube.*—Closed.

*Styles.*—8.0 mm.

*Axillary cavity.*—Middle-deep to deep.

*Seed cells.*—Wall: Firm. Depth: 12.0 mm. Breadth: 5.0–6.0 mm.

Seeds:

*Number perfect.*—10 to 14 (very fertile).

*Number in one cell.*—2–3.

*Length.*—7.0—8.0 mm.

*Breadth.*—2.5–3.0 mm.

*Form.*—Oblong to ovoid.

*Color.*—166A to 166B, up to 200D.

*Locules* (*closed*).—Length: 10.5 mm. Width: 5–8 mm.

*Position.*—Mostly free from the carpel wall.

Stem:

*Length.*—Average of 40.0 mm (range of 35.0–45.0 mm).

*Width.*—Average of 1.4 mm.

*Color.*—Initially 172B, changing to 199A.

Use: Table fruit; high quality dessert apple; long storage time.

Shipping quality: Excellent and firm, no bruising with normal handling.

Keeping quality: Excellent; apples last from 5 to 7 months on average; needs more than 90% (optimum 96%) humidity.

Tree winter hardiness: Hardy to −25° C. under weather conditions typical in Germany (hardier than 'Jonagold').

Bud winter hardiness: Hardy to −25° C. under weather conditions typical in Germany (hardier than 'Elstar' (U.S. Plant Pat. No. 6,450)).

Drought tolerance: Minimal, because the small fruits need irrigation under dry conditions.

Disease resistance: Low susceptibility to scab; medium susceptibility to powdery mildew and fire blight; sometimes *Gloeosporium* rot occurs in storage.

I claim:

1. A new and distinct variety of *Malus domestica Borkh.* tree substantially as shown and described.

* * * * *

UNITED STATES PATENT AND TRADEMARK OFFICE

CERTIFICATE OF CORRECTION

PATENT NO. : PP 17,672 P3
APPLICATION NO. : 11/100366
DATED : May 1, 2007
INVENTOR(S) : Hofmann It is certified that error appears in the above-identified patent and that said Letters Patent is hereby corrected as shown below:

Column 2, Lines 14-15, “rootstock is 1.8 cm” should read -- rootstock is 1.8 m --

Column 2, Line 20, “Spindle bus;” should read -- Spindle bush; --

Column 3, Line 62, “second weak” should read -- second week --

Signed and Sealed this

Ninth Day of October, 2007

JON W. DUDAS
*Director of the United States Patent and Trademark Office*